United States Patent [19]

Pearson

[11] Patent Number: 5,118,832

[45] Date of Patent: Jun. 2, 1992

[54] PROCESS FOR THE PREPARATION OF ALKYL 3-CHLOROANTHRANILATES

[75] Inventor: Norman R. Pearson, Walnut Creek, Calif.

[73] Assignee: DowElanco, Indianapolis, Ind.

[21] Appl. No.: 715,514

[22] Filed: Jun. 14, 1991

[51] Int. Cl.$^5$ ............................................ C07C 229/00
[52] U.S. Cl. ..................................................... 560/47
[58] Field of Search .......................................... 560/47

[56] References Cited

PUBLICATIONS

Gutsche et al., *Fundamentals of Organic Chemistry*, Prentice-Hall, Englewood Cliffs (1975), pp. 960–969.

*Primary Examiner*—Bruce Gray
*Attorney, Agent, or Firm*—Craig E. Mixan

[57] ABSTRACT

Alkyl 3-chloroanthranilates are the major product from the chlorination of alkyl esters of anthranilic acid with 1,3-dichloro-5,5-dimethylhydantoin. The 3-chloro isomer can be readily separated from the accompanying 5-chloro isomer by selective acetylation of the latter.

4 Claims, No Drawings

PROCESS FOR THE PREPARATION OF ALKYL 3-CHLOROANTHRANILATES

FIELD OF THE INVENTION

The present invention concerns a process for preparing alkyl esters of 3-chloroanthranilic acid by the chlorination of the corresponding esters of anthranilic acid. More particularly, the present invention concerns the selective chlorination of alkyl anthranilates with 1,3-dichloro-5,5-dimethylhydantoin.

BACKGROUND OF THE INVENTION

Alkyl 3-chloroanthranilates are useful intermediates in the manufacture of a variety of chemical products including agricultural chemicals: see, for example, U.S. Pat. No. 4,954,163.

The direct chlorination of anthranilates to the 3-chloro isomer has not been very successful. Chlorination of methyl anthranilate with molecular chlorine, for example, gives predominantly methyl 5-chloroanthranilate with substantial amounts of dichlorination. N-Chlorosuccinimide has been used as a chlorinating agent for various substrates but with very unpredictable results as to the product and by-product ratios obtained. The use of N-chlorosuccinimide to chlorinate aniline and N-alkyl or ring alkyl anilines has led to the production of p-chlorinated anilines or to mixtures of o- and p-chlorinated anilines; see, for example, N. Buu-Hoi, J. Chem. Soc, 2815 (1958); T. Chao, J. Org. Chem., 26, 1079 (1961); R. Neale, J. Org. Chem., 29, 3390 (1964): and D. Paul, J. Org. Chem., 41, 3170 (1976). Although some ortho chlorination is obtained, substantial amounts of para chlorination also prevail.

Because of this unpredictability with respect to electrophilic halogenations, other approaches to alkyl 3-chloroanthranilates are usually advocated. For example, U.S. Pat. No. 4,306,074 discloses the preparation of a mixture of alkyl 3-chloroanthranilate and alkyl 6-chloroanthranilate in a 3:1 ratio from 3-chlorophthalic anhydride by amination, Hofmann degradation and esterification.

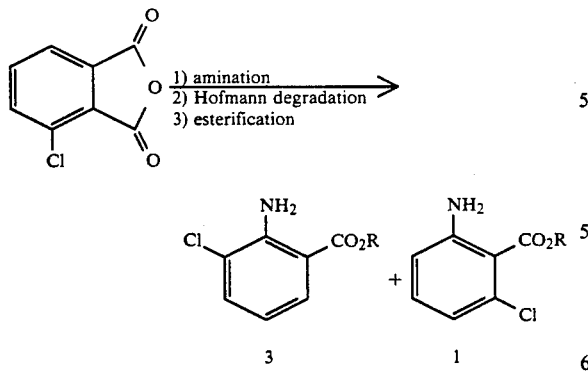

This procedure entails three discrete steps, not including separation of the resultant mixture, after chlorine has been introduced into the starting material. It would be desirable to have a process in which an alkyl 3-chloroanthranilate could be obtained in high proportion to other less desirable isomers directly from the corresponding alkyl anthranilate.

SUMMARY OF THE INVENTION

The present invention concerns a process for the preparation of alkyl esters of 3-chloroanthranilic acid of the Formula

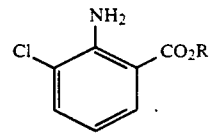

wherein
R is a straight-chain or branched-chain alkyl group of from 1 to 4 carbon atoms
which comprises reacting an alkyl ester of anthranilic acid of the Formula

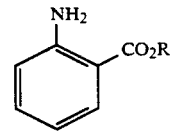

wherein
R is as previously defined
with 1,3-dichloro-5,5-dimethylhydantoin in an inert solvent at a temperature from 0° to about 150° C., and separating the alkyl 3-chloroanthranilate from the mixture.

Another aspect of the invention concerns a process for the isolation of the 3-chloroanthranilate ester from the by-product 5-chloroanthranilate ester by the selective acetylation and removal of the 5-chloroanthranilate.

Thus, the present invention allows for the preparation and isolation of alkyl esters of 3-chloroanthranilic acid as the major product from the chlorination of alkyl anthranilates.

DETAILED DESCRIPTION OF THE INVENTION

The lower alkyl esters of anthranilic acid, which are the starting materials for the present invention, are known compounds and are commercially available. Similarly, 1,3-dichloro-5,5-dimethylhydantoin (DDH) is also readily available.

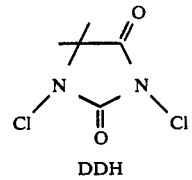

DDH

DDH is capable of delivering two equivalents of chlorine per mole of reagent. Thus, from about 0.4 to about 0.75 molar equivalents of DDH are employed per equivalent of anthranilate; from about 0.45 to about 0.6 equivalents of DDH are preferred.

The chlorination is generally performed in a solvent that is inert to the reaction conditions, such as aliphatic and aromatic hydrocarbons or halogenated hydrocarbons. The most suitable inert solvents for use in the process of this invention are halogenated hydrocarbons such as the halogenated alkanes, e.g., $CCl_4$, $CHCl_3$, $CH_2Cl_2$, $C_2Cl_4$, etc. Perchloroethylene is most preferred.

The amount of solvent is not critical, but improved selectivity to the 3-chloroanthranilate can be achieved in more dilute solutions. This advantage, however, must be weighed against the cost of recovering and recycling increased amounts of solvent. For example, under certain conditions, by decreasing the concentration of anthranilate from about 5 to about 1 weight percent, the proportion of 3-chloroanthranilate in the final reaction mixture can be increased from about 56 to about 70 percent. Generally from about 5 to about 100 parts by weight of solvent per part by weight of anthranilate are employed.

The chlorination is conducted at temperatures ranging from 0° to about 150° C. Often it is convenient to conduct the reaction at the reflux temperature of the solvent. This is particularly so for the preferred solvents carbon tetrachloride and perchloroethylene.

The chlorination invariably gives rise to a reaction mixture containing 3-chloroanthranilate together with varying amounts of 5-chloroanthranilate and 3,5-dichloroanthranilate.

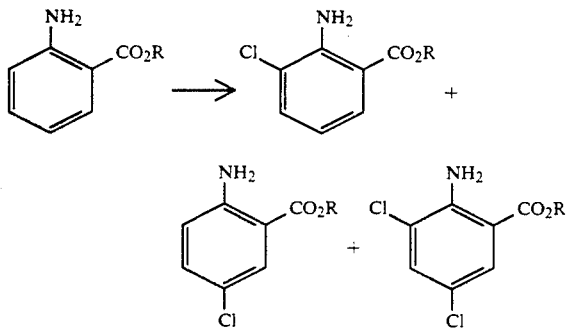

Even though the present invention provides the alkyl 3-chloroanthranilate as the predominant product, it still must be separated from the mixture. In order to facilitate the isolation of the alkyl 3-chloroanthranilate from the mixture, the less desirable 5-chloro isomer can be selectively acetylated and separated on the basis of its now substantially different physical properties, such as the differences in solubility or volatility. For example, by treating the reaction mixture with from about 1.0 to about 1.2 equivalents of acetic anhydride per mole of 5-chloroanthranilate present in the reaction mixture, the 5-chloro isomer is selectively converted into an acetanilide which is insoluble in hydrocarbon solvents.

Thus, the present invention can be carried out according to the following preferred embodiment. The alkyl anthranilate, 1,3-dichloro-5,5-dimethylhydantoin (DDH) and chlorinated hydrocarbon solvent are stirred at elevated temperature until the chlorination is complete. The reaction mixture is then treated with enough acetic anhydride to acetylate the 5-chloroanthranilate in the reaction mixture. After cooling, the mixture is filtered to remove 5,5-dimethylhydantoin from the spent DDH. The dimethylhydantoin can be chlorinated back to DDH and recycled in the process. The solvent is evaporated from the filtrate and the residue is slurried with a hydrocarbon solvent. The solid alkyl N-acetyl-5-chloroanthranilate is removed by filtration and the filtrate is again concentrated. The alkyl 3-chloroanthranilate is recovered from the organic concentrate and separated from the 3,5-dichloroanthranilate by vacuum distillation.

The following examples illustrate the practice of the invention and should not be construed as limiting.

EXAMPLE 1

A solution of 0.50 gram (g) (3.3 mmol) of methyl anthranilate and 8 mL of carbon tetrachloride was treated at room temperature with 0.36 g (1.8 mmol) of 1,3-dichloro-5,5-dimethylhydantoin (DDH) and the resulting mixture was heated at reflux for 24 hours (hr) After cooling, the mixture was partitioned between ether and water, and the organic phase was analyzed by gas chromatography (GC): methyl anthranilate 8.7 percent, methyl 3-chloroanthranilate 46.1 percent, methyl 5-chloroanthranilate 33.5 percent and methyl 3,5-dichloroanthranilate 1.8 percent.

EXAMPLE 2

The procedure of Example 1 was repeated using perchloroethylene as the solvent. Reaction temperature and concentration were varied. The results are summarized in Table I.

TABLE I

Chlorination of Methyl Anthranilate with 1,3-Dichloro-5,5-dimethylhydantoin in Perchloroethylene at Various Concentrations and Temperatures

| Reactor Loading (wt. % MA) | Temperature (°C.) | Selectivity (%) | | |
|---|---|---|---|---|
| | | 3-Cl | 5-Cl | 3,5-DiCl |
| 10.0 | 95 | 44.4 | 48.5 | 4.9 |
| 5.0 | 121 | 56.0 | 39.6 | 4.4 |
| 3.6 | 121 | 60.0 | 36.0 | 4.0 |
| 3.6 | 85 | 57.6 | 39.2 | 3.1 |
| 1.0 | 121 | 70.3 | 23.5 | 6.2 |

EXAMPLE 3

A solution of 100.0 g (661.5 mmol) of methyl anthranilate and 1130 mL of perchloroethylene was treated at room temperature with 68,42 g (347.3 mmol) of 1,3-dichloro-5,5-dimethylhydantoin, and the resulting mixture was heated to reflux over 50 minutes and was then held at reflux for two hours. After cooling to ° C., 31.3 mL (331 mmol) of acetic anhydride was added and the mixture was heated at reflux for 30 minutes. After cooling to room temperature, the solid present (5,5-dimethylhydantoin) was removed by filtration and the filtrate was concentrated under vacuum to afford 134.6 g of a dark solid. This material was stirred in 600 mL of hexane for 30 minutes to afford, after filtration and air drying, 54.5 g (36 percent crude) of methyl N-acetyl-5-chloroanthranilate. The filtrate was concentrated under vacuum to 78.5 g of a dark, amber oil that was purified by vacuum distillation to furnish 60.8 g (49.6 percent) of an oil that solidified on standing, b.p. 80°-85° C. (0.1 mm), m.p. 33°-35° C.: $^1$H NMR (CDCl$_3$) δ7.80 (1H, d, J=8 Hz, 6-H), 7.40 (1H, d, J=8 Hz, 4-H), 6.58 (1H, t, J=8 Hz, 5-H), 6.26 (2H, broad s, —NH$_2$) and 3.88 (3H, s, —CH$_3$).

What is claimed is:

1. A process for the preparation of alkyl esters of 3-chloroanthranilic acid of the Formula

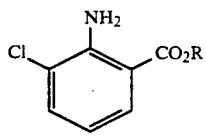

wherein

R is a straight-chain or branched-chain alkyl group of from 1 to 4 carbon atoms which comprises reacting an alkyl ester of anthranilic acid of the Formula

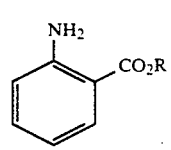

wherein

R is as previously defined with 1,3-dichloro-5,5-dimethylhydantoin in an inert solvent at a temperature from 0° to about 150° C., and separating the alkyl 3-chloroanthranilate from the mixture.

2. The process of claim 1 in which the inert solvent is a halogenated hydrocarbon solvent.

3. A process for the separation of alkyl 3-chloroanthranilates from the corresponding 5-chloroanthranilates which comprises contacting the alkyl 5-chloroanthranilate in admixture with the alkyl 3-chloroanthranilate with from 1.0 to 1.2 equivalents of acetic anhydride per equivalent of 5-chloroanthranilate under conditions which give a mixture of alkyl N-acetyl-5-chloroanthranilate and alkyl 3-chloroanthranilate and separating the acetylated 5-chloro isomer from the non-acetylated 3-chloro isomer.

4. The process of claim 3 in which the separation is achieved on the basis of differences in solubility.

* * * * *